US009078760B2

(12) United States Patent
Marshall

(10) Patent No.: US 9,078,760 B2
(45) Date of Patent: *Jul. 14, 2015

(54) DEVICES FOR CONCEALING A URINE COLLECTION BAG AND THAT PROVIDE ACCESS TO MONITOR AND MANIPULATE A URINE COLLECTION BAG THEREIN

(71) Applicant: MARY MARSHALL ENTERPRISES, INC., Gainesville, FL (US)

(72) Inventor: Mary L. Marshall, Gainesville, FL (US)

(73) Assignee: MARY L. MARSHALL ENTERPRISES, INC., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/748,673

(22) Filed: Jan. 24, 2013

(65) Prior Publication Data

US 2014/0207093 A1 Jul. 24, 2014

Related U.S. Application Data

(63) Continuation-in-part of application No. 12/420,158, filed on Apr. 8, 2009, now Pat. No. 8,361,044, which is a continuation-in-part of application No. 29/305,137, filed on Mar. 14, 2008, now Pat. No. Des. 618,340.

(51) Int. Cl.
*A61F 5/44* (2006.01)
*A61F 5/445* (2006.01)
(Continued)

(52) U.S. Cl.
CPC ............... *A61F 5/4408* (2013.01); *A61F 5/44* (2013.01); *A61F 5/4404* (2013.01); *A61F 5/445* (2013.01);
(Continued)

(58) Field of Classification Search
CPC ......... A61F 5/4408; A61F 5/44; A61F 5/445; A61F 5/449; A61F 5/4405; A61F 5/4404; A61F 5/451; A61F 5/453; A61F 5/455; Y10S 128/24; A61M 1/0019; A61M 25/0017; A61M 25/002; A61M 2202/0496; A61G 7/0503
USPC ................ 604/327, 353, 332, 351, 329, 326; 383/66, 103, 106, 61.1, 63
See application file for complete search history.

(56) References Cited

U.S. PATENT DOCUMENTS 2,662,525 A 12/1953 Priebe
3,471,871 A * 10/1969 Nociti et al. ................ 4/484
(Continued)

FOREIGN PATENT DOCUMENTS

JP 2004-081282 3/2004
WO WO 86/05969 10/1986

OTHER PUBLICATIONS

Cypress Medical Products product information [online, webpage, retrieved Apr. 17, 2008] retrieved from: http://www.cypressmed.com/ancillary.html, pp. 1-2.
(Continued)

*Primary Examiner* — Leslie Deak
*Assistant Examiner* — Kai Weng
(74) *Attorney, Agent, or Firm* — Saliwanchik, Lloyd & Eisenschenk

(57) ABSTRACT

A cover for concealing and supporting a urinary incontinence bag to be worn by an individual in conjunction with a catheter and attached tubing. The cover provides a comfortable sleeve for containing the urinary bag and one or more straps for securing the bag to the leg of an individual. Additional features include a covered sleeve window for monitoring the urine bag contents and a collar for increased wearing comfort and support of the tubing. An outflow valve cover is also disclosed for concealing and protecting the outflow valve.

20 Claims, 11 Drawing Sheets

(51) Int. Cl.
*A61F 5/449* (2006.01)
*A61F 5/451* (2006.01)
*A61F 5/455* (2006.01)
*A61M 1/00* (2006.01)
*A61M 25/00* (2006.01)
*A61G 7/05* (2006.01)

(52) U.S. Cl.
CPC ............... *A61F 5/449* (2013.01); *A61F 5/451* (2013.01); *A61F 5/455* (2013.01); *A61G 7/0503* (2013.01); *A61M 1/0019* (2013.01); *A61M 25/0017* (2013.01); *Y10S 128/24* (2013.01)

(56) References Cited

U.S. PATENT DOCUMENTS

| | | |
|---|---|---|
| 3,570,490 A | 3/1971 | Berger |
| 3,897,785 A | 8/1975 | Barto |
| 4,122,851 A | 10/1978 | Grossner |
| 4,173,979 A | 11/1979 | Odis |
| 4,511,358 A | 4/1985 | Johnson, Jr. et al. |
| 4,519,797 A * | 5/1985 | Hall ........................ 604/332 |
| 4,533,355 A | 8/1985 | Fair |
| 4,606,736 A | 8/1986 | Van De Weghe |
| 4,705,512 A | 11/1987 | Faucher |
| 4,874,387 A | 10/1989 | Boone |
| 4,938,747 A | 7/1990 | Wallace |
| 4,955,879 A | 9/1990 | Mervine |
| D316,602 S | 4/1991 | Dungan et al. |
| 5,032,118 A | 7/1991 | Mason |
| 5,087,251 A | 2/1992 | Heyman et al. |
| 5,193,553 A * | 3/1993 | Kalinoski ..................... 600/580 |
| 5,215,379 A | 6/1993 | Pickard et al. |
| 5,234,420 A | 8/1993 | Horton et al. |
| 5,267,987 A | 12/1993 | Fabricant |
| 5,392,973 A | 2/1995 | Benson |
| 5,439,456 A | 8/1995 | Fabricant |
| 5,531,724 A | 7/1996 | Young et al. |
| 5,643,236 A | 7/1997 | Hadley |
| 5,653,701 A | 8/1997 | Millman |
| 5,700,257 A | 12/1997 | Minick et al. |
| 5,759,180 A | 6/1998 | Myhres |
| 5,865,819 A | 2/1999 | Cisko et al. |
| 5,961,501 A | 10/1999 | Cassidy et al. |
| D438,616 S | 3/2001 | Williams |
| 6,887,223 B2 | 5/2005 | Bisbee |
| 7,691,091 B1 * | 4/2010 | Baggett ........................ 604/317 |
| 2002/0077609 A1 | 6/2002 | Johnson |
| 2003/0121194 A1 | 7/2003 | Rappaport et al. |
| 2004/0006321 A1 * | 1/2004 | Cheng et al. .................. 604/349 |
| 2004/0204695 A1 | 10/2004 | Bisbee |
| 2004/0215158 A1 | 10/2004 | Anderson |
| 2004/0261159 A1 | 12/2004 | Reilly et al. |
| 2005/0261645 A1 | 11/2005 | Conrad et al. |
| 2006/0224130 A1 | 10/2006 | Garrett |
| 2006/0253091 A1 | 11/2006 | Vernon |
| 2006/0258997 A1 | 11/2006 | Belt |
| 2006/0293630 A1 * | 12/2006 | Manna et al. ................. 604/327 |
| 2006/0293631 A1 | 12/2006 | Bolt |
| 2007/0208314 A1 | 9/2007 | Barrientos |
| 2007/0260208 A1 | 11/2007 | May |
| 2008/0004560 A1 | 1/2008 | Miskie |
| 2008/0047990 A1 | 2/2008 | Morgan et al. |
| 2008/0140034 A1 | 6/2008 | Edling |
| 2008/0269700 A1 | 10/2008 | O'Toole et al. |
| 2009/0112171 A1 | 4/2009 | Ng et al. |
| 2009/0234310 A1 * | 9/2009 | Marshall ........................ 604/327 |
| 2009/0247970 A1 | 10/2009 | Keleny et al. |

OTHER PUBLICATIONS

Secure Urinary Leg Bag Holders product information [online, webpage, retrieved Apr. 17, 2008] retrieved from: http://www.llmedico.com/urine-bag-holders/ p. 1.

Urine Bag One Leg Stocking product information [online, webpage, retrieved Apr. 17, 2008] retrieved from: http://www.llmedico.com/n/one-leg-stocking/ p. 1.

Urine Bag Holder One Leg Pants product information [online, webpage, retrieved Apr. 17, 2008] retrieved from: http://www.llmedico.com/n/one-leg-pants/ p. 1.

Shield Healthcare Leg Bag Holder product information [online, webpage, retrieved Apr. 17, 2008] retrieved from: http://www.shieldhealthcare.com, p. 1.

* cited by examiner

DEVICES FOR CONCEALING A URINE COLLECTION BAG AND THAT PROVIDE ACCESS TO MONITOR AND MANIPULATE A URINE COLLECTION BAG THEREIN

CROSS-REFERENCE TO RELATED APPLICATIONS

The present application is a continuation-in-part of U.S. Pat. No. 8,361,044, filed Apr. 8, 2009, which is a continuation-in-part of U.S. Design Pat. No. D618,340, filed Mar. 14, 2008.

BACKGROUND OF INVENTION

It is an unfortunate reality that individuals afflicted with certain urological-related illnesses or diseases can be further burdened with the discomfort of urinary incontinence. Urinary incontinence can result when the urinary tract is blocked or weakened to the point that it loses its ability to retain natural urine flow. In such cases, individuals can be fitted with a urinary catheter, condom catheter, inter-urethral catheter, or other urine collection apparatus that is connected, via an extension tube, to a urine collection bag.

Urine collection bags are available in a variety of sizes and styles. Many are designed to be attached to a nearby chair or table, or on a rolling stand. For individuals that are ambulatory, or are otherwise able to move about, it can be preferable to utilize a urine bag style that straps to the body, such as the leg, rather than one that must be held or supported by other means. In fact, current medical protocols often encourage individuals who undergo most procedures to become ambulatory as soon as possible. This can facilitate healing and a return to normal bodily functions. Thus, individuals experiencing incontinence after a procedure are often provided with urine bag systems. Urine bag systems include a urine collection bag, usually made of disposable plastic, vinyl, or other waterproof material, that can be strapped to the body, usually the upper thigh. Urine is collected through a tube and deposited through an inlet port somewhere in the top portion of the leg-strapped bag. The urine bag can be periodically drained through some type of release valve, most often located at the bottom of the bag.

While these leg-strapped urine bag systems can facilitate movement, they can also be uncomfortable, as well as a source of embarrassment, anxiety, and emotional stress for individuals who have to wear them in public. Typical urine bags usually afford little or no concealment of the contents. While they can be worn under certain types of clothing, it may not be practical to wear long pants or skirts in warmer climates to conceal the bag and contents. The bags are also designed to be emptied periodically, which can be difficult to do if they are positioned under clothing. Furthermore, positioning of the bag or the supporting bands against the skin often causes irritation, itching, sweating, and chafing, which is often exacerbated as the bag fills.

In many circumstances, it may also be necessary to monitor urine flow into the bag. Knowing whether sufficient or too much urine is being excreted, whether the urine has a normal color, detecting blood or other abnormalities, or just checking the fullness of the bag require being able to see the bag and contents. Again, concealing the bag under long clothing or in complicated concealing covers can make it problematic to monitor the urine flow.

Another issue to contend with is movement of the tubing between the individual and the urine bag. Movement of the catheter or other urine collection apparatus in or near the body can cause considerable pain. Further, movement of internal catheters can lead to infection of the urinary tract and/or the bladder if bacteria on the tubing are accidentally introduced into the urinary tract.

Many devices have been designed to conceal urine collection bags that reduce irritation and/or restrict movement of the tubing. Unfortunately, many of the devices are uncomfortable and can be complicated or difficult to use. Some, in an effort to provide stability against the leg and restrict movement of the tubing, utilize a full leg cover or a blouse- or shirt-like garment that must be worn to support the bag. Others, while simpler to use do not cover the bag completely or do not provide easy access to the view the bag contents.

It seems apparent that a urine bag cover is needed that is easy to use, conceals most or all of the bag and/or contents therein, and improves the comfort for the wearer. It should also provide a convenient way to view the contents of the bag while maintaining individual privacy. The ability to reduce or eliminate excessive movement of the tubing will also be beneficial. Further, improving the look of the cover with decorative features or attractive material(s) can also reduce the embarrassment and anxiety of the wearer and allow one to wear the bag outside of clothing fir more convenience.

BRIEF SUMMARY

The subject application describes a urine bag cover to be worn by an individual either under or over clothing. More specifically, the subject application describes a urine bag cover that can conceal and support the bag against the leg of an individual. The urine bag cover as described provides full concealment, and in certain embodiments also employs a covered opening through which the urine bag and contents can be conveniently monitored, as necessary, without removal from the cover or otherwise compromising the privacy of the individual.

In general, the urine bag cover of the subject invention is a sleeve, into which a urine bag can be easily inserted, with one or more attached straps or other securing devices tier fixing the cover against the body, such as the leg, of an individual. The sleeve includes at one end an opening of sufficient width to easily insert and remove a urine bag, as well as an orifice at another end to accommodate the drain valve frequently provided on urine bags. A coverable opening in the sleeve allows one to monitor the contents of a urine bag housed within the sleeve without the bag's removal and with minimal manipulation of the sleeve within the cover.

Other embodiments also disclosed herein include accessories or attachments for the cover that can assist with stability of the tubing between the bag and the catheter or other urine collection apparatus in contact with the individual. One accessory allows a portion of the tubing to be secured to the leg, which can reduce or eliminate pushing, pulling, bouncing, or other extraneous movements of the tube and the attached urine collection apparatus.

The urine bag cover of the subject invention provides an easy, discreet way for an individual to wear a urine bag with less physical discomfort and emotional stress. The cover of the subject invention allows a urine bag and contents to be easily monitored and drained without removal from the cover. The cover can also assist with securing the associated urine bag tubing to reduce discomfort and infections.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. It should also be understood that the drawings presented herein may not be drawn to scale and that any reference to dimensions in the drawings or the following description are specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings which:

FIGS. 4A and 4B show the sleeve flap closed. FIGS. 4C and 4D show the sleeve flap open.

DETAILED DISCLOSURE

Figure 1:
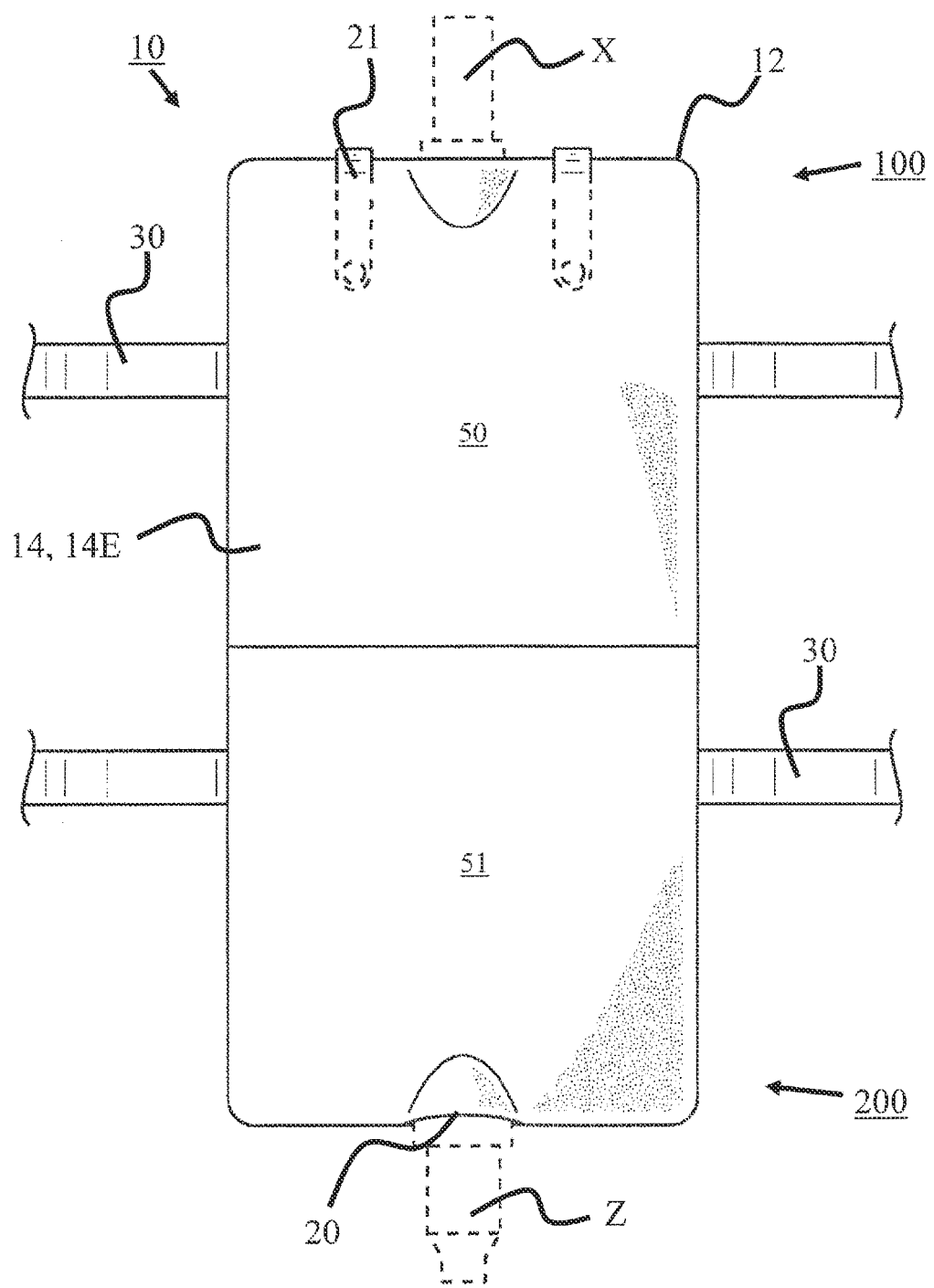
FIG. 1 is an illustration of a front elevational view of one embodiment of the subject invention, wherein the sleeve flap is closed.

The subject invention in general pertains to embodiments of a urine bag cover. More specifically, the subject invention pertains to one or more embodiments of a urine bag cover that can be worn by an individual. The cover is capable of providing visual monitoring of the urine bag while maintaining the bag in the cover. The subject invention also provides a method and accessories or attachments that can be used to support the associated urine bag tubing.

The following description will disclose that the subject invention is particularly useful for covering or concealing urinary leg bags. The subject invention is particularly useful for covering urine leg bags used by individuals suffering incontinence, but who are ambulatory or otherwise able to move around or are not necessarily bed-ridden. However, a person with skill in the art will be able to recognize numerous other uses that would be applicable to the devices and methods of the subject invention. While the subject application describes a use for covering and/or concealing urine bags, other modifications apparent to a person with skill in the art and having benefit of the subject disclosure are contemplated to be within the scope of the present invention.

As used herein, and unless otherwise specifically stated, the terms "operable communication" and "operably connected" mean that the particular elements are connected in such a way that they cooperate to achieve their intended function or functions. The "connection" may be direct, indirect, permanent, non-permanent, physical, or remote.

Also, the term "body" as used in the subject application is merely for literary convenience. It should be understood that the embodiments of the subject invention can be used on any area of an individual, including, but not limited to, the torso, arms and upper and lower legs, it should also be understood that while the subject application describes a urine bag cover that facilitates attachment to an individual, the cover could also be used to attach a urine bag to something other than an individual, if so desired.

In addition, references to "first", "second", and the like (e.g., first and second opening), as used herein, and unless otherwise specifically stated, are intended to identify a particular feature of which there are at least two. However, these references are not intended to confer any order in time, structural orientation, or sidedness (e.g., left or right) with respect to a particular feature.

The present invention is more particularly described in the following embodiments that are intended to be illustrative only since numerous modifications and variations therein will be apparent to those skilled in the art. As used in the specification and in the claims, the singular for "a," "an" and "the" include plural referents unless the context clearly dictates otherwise.

It should also be understood that any reference in this application to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. Further, when a particular feature, structure, or characteristic is described in connection with any embodiment, it is submitted that it is within the purview of one skilled in the art to affect such feature, structure, or characteristic in connection with other ones of the embodiments.

Figure 2:
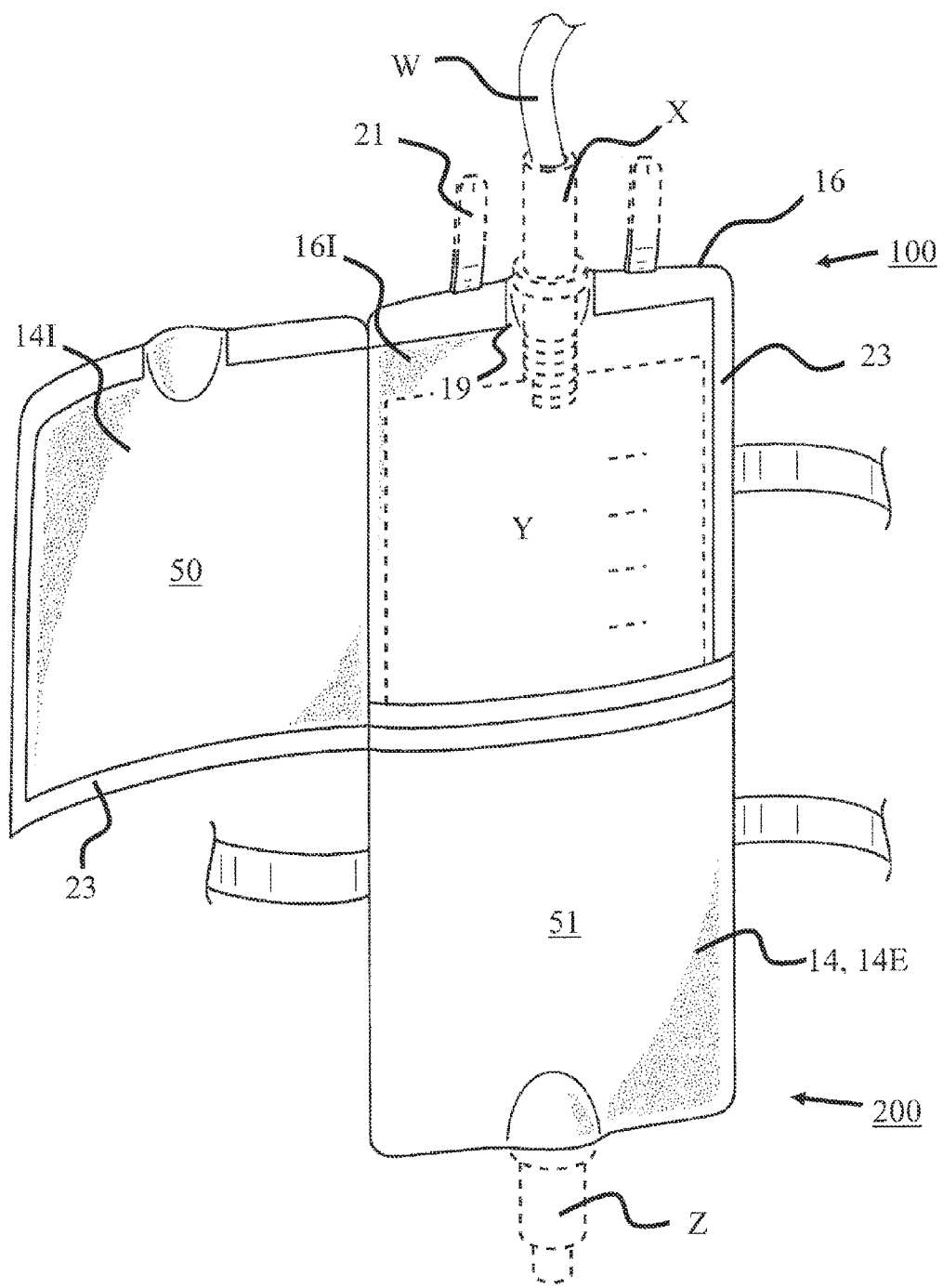
FIG. 2 is an illustration of a front perspective view of the embodiment shown in FIG. 1, wherein the sleeve flap is open to show a urine bag cover (dotted lines) therein.
Figure 3:
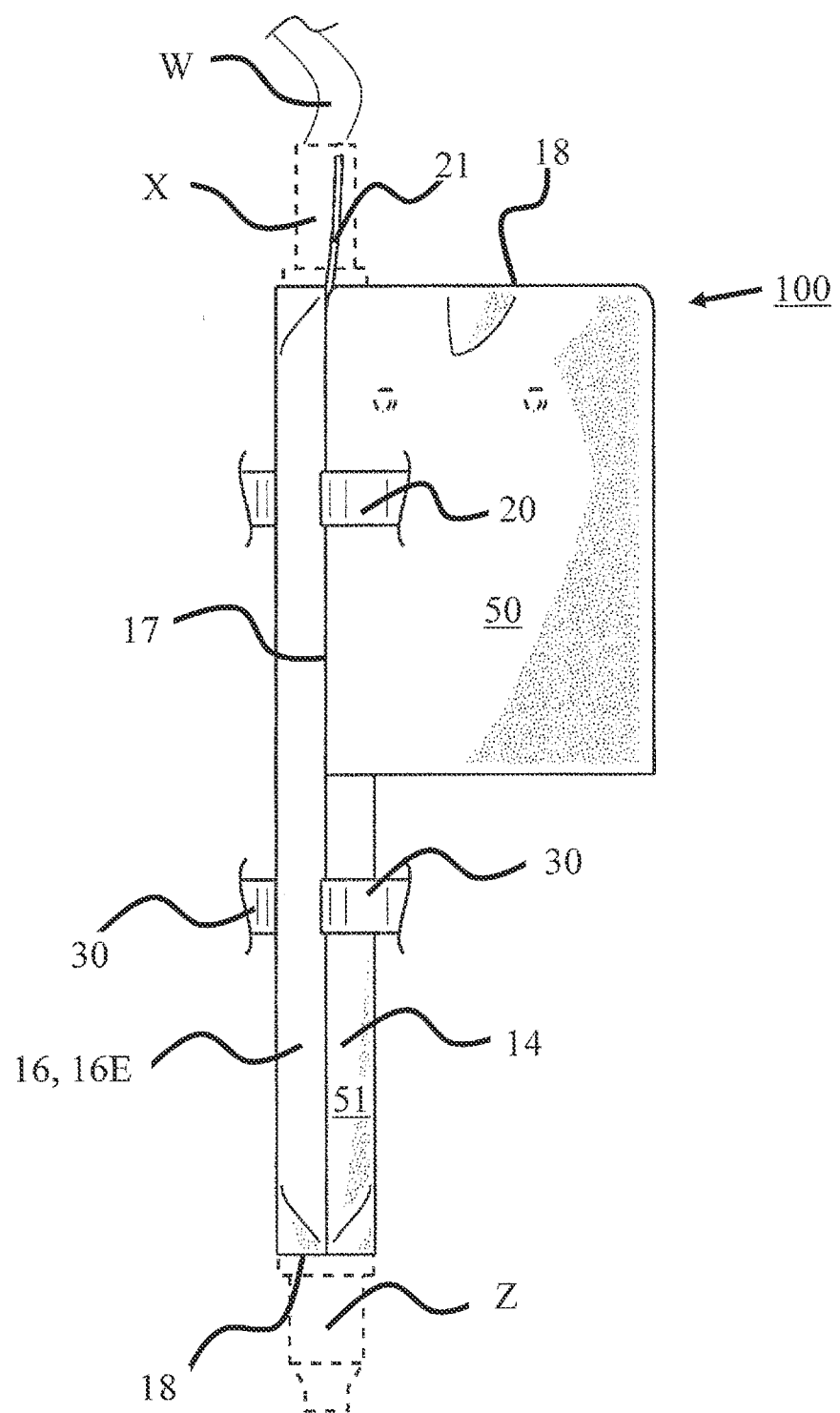
FIG. 3 is an illustration of side elevational view of the embodiment shown in FIG. 2.

With reference to the attached figures, which show certain embodiments of the subject invention, it can be seen in FIG. 1 that the subject invention is in general a cover 10 for a urine bag Y (shown as dotted lines in the figures) or similar device where the urine bag Y is contained within a sleeve 12. As seen in the embodiment of FIGS. 2 and 3, the sleeve can have a front face 14 with an interior side 14I and an exterior side 14E and a rear face 16, also having an interior side 16I and an exterior side 16E. In one embodiment the front face 14 and the rear face 16 are separate components that are operably attached at or near at least some portion of their side edges 17 or end edges 18. In an alternative embodiment, the front face and rear face are a single or almost single component.

The urine bag can be placed within the sleeve and the sleeve can be secured to the body of an individual, as will be described below. To facilitate insertion of the urine bag, the proximal end 100 of the sleeve is formed with a sleeve slot 15 through which the urine bag can be passed into the sleeve interior 75. In one embodiment, the sleeve slot 15 has dimensions that are approximately equivalent to the width of a urine bag, allowing the bag to be inserted without appreciable deformation. In this embodiment, shown for example, in FIG. 4C, the slot 15 is generally the same width as the width of the sleeve, so the urine bag can be easily inserted without substantial change to the native form. In an alternative embodiment, the slot 15 has dimensions that are smaller than the width of a urine bag, such that insertion of the urine bag requires folding, bending, crumpling or some other type of deformation to be inserted into the sleeve interior.

Figure 10:
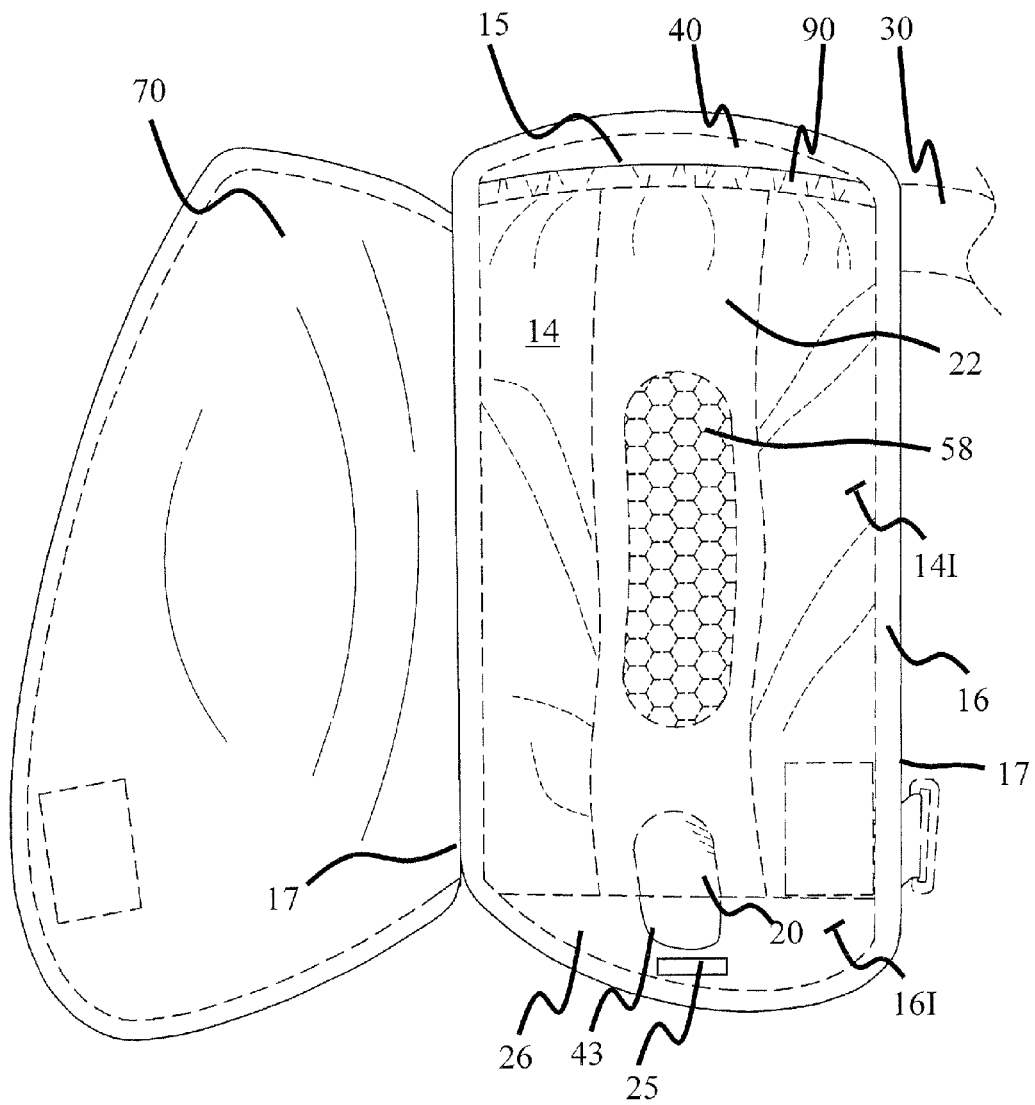
FIG. 10 is an illustration of a front elevation view of an alternative embodiment of a urine bag cover having a front face cover, according to embodiments of the subject invention. In this view, the front face cover is folded back to show the front face of the sleeve and other features of the cover.

Because a urine bag will expand as it fills, it can be beneficial if the sleeve is capable of accommodating the increase in size and volume. To accommodate for this increase in size and volume of a urine bag, the front face 14, or some portion thereof, can comprise one or more materials or can have one or more structures that allow it to expand. In one embodiment, the front face, or some portion thereof, can comprise a deformable or pliable material that can stretch and expand as a urine bag fills. In another embodiment, the front face, or some portion thereof, can comprise components or structural features 22 that allow the front face to expand. By way of non-limiting example, a front face can comprise one or more pleats, folds, or tucks that can allow the material of the front face 14 to protrude or expand outward as a urine bag fills. FIG. 10 illustrates one embodiment of a sleeve 12 having structural features 22 that provide an expandable front face 14.

Figure 4A:
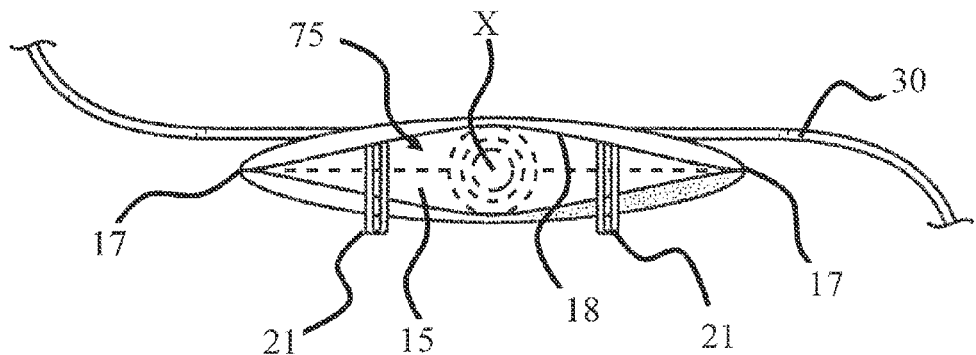
FIGS. 4A, 4B, 4C, and 4D illustrate top plan views (4A and 4C) and bottom plan (4B and 4D) views of embodiments of the subject invention.

Once the urine bag Y has been inserted, it is important that it be securable within the sleeve, so as to not slide out unexpectedly. In one embodiment, one or more security tabs 21 can cross over the slot 15, in a suspender-like fashion, and act as a barrier, to prevent the bag inside from sliding out or the cover from sliding off the bag. Security tabs are basically elongated or slightly elongated devices with a first and second end, where the first end is attached to the front face exterior 14E, at or near the slot 15 and the second end is attached to the rear face exterior 16E, again, at or near the slot, such that the security tab 21 goes over the slot. The attachment of the security tabs can be permanent or removable. In a specific embodiment, the first end is removably and/or adjustably attached to the front face exterior 14E and the second end is fixedly attached to the rear face exterior 16E. Examples of security tabs 21 that can be used with the subject invention are shown in FIGS. 1, 2, and 4A. In alternative embodiments, the ends of a security tab are attached to the front face interior and/or the rear face interior, respectively.

Figure 6:
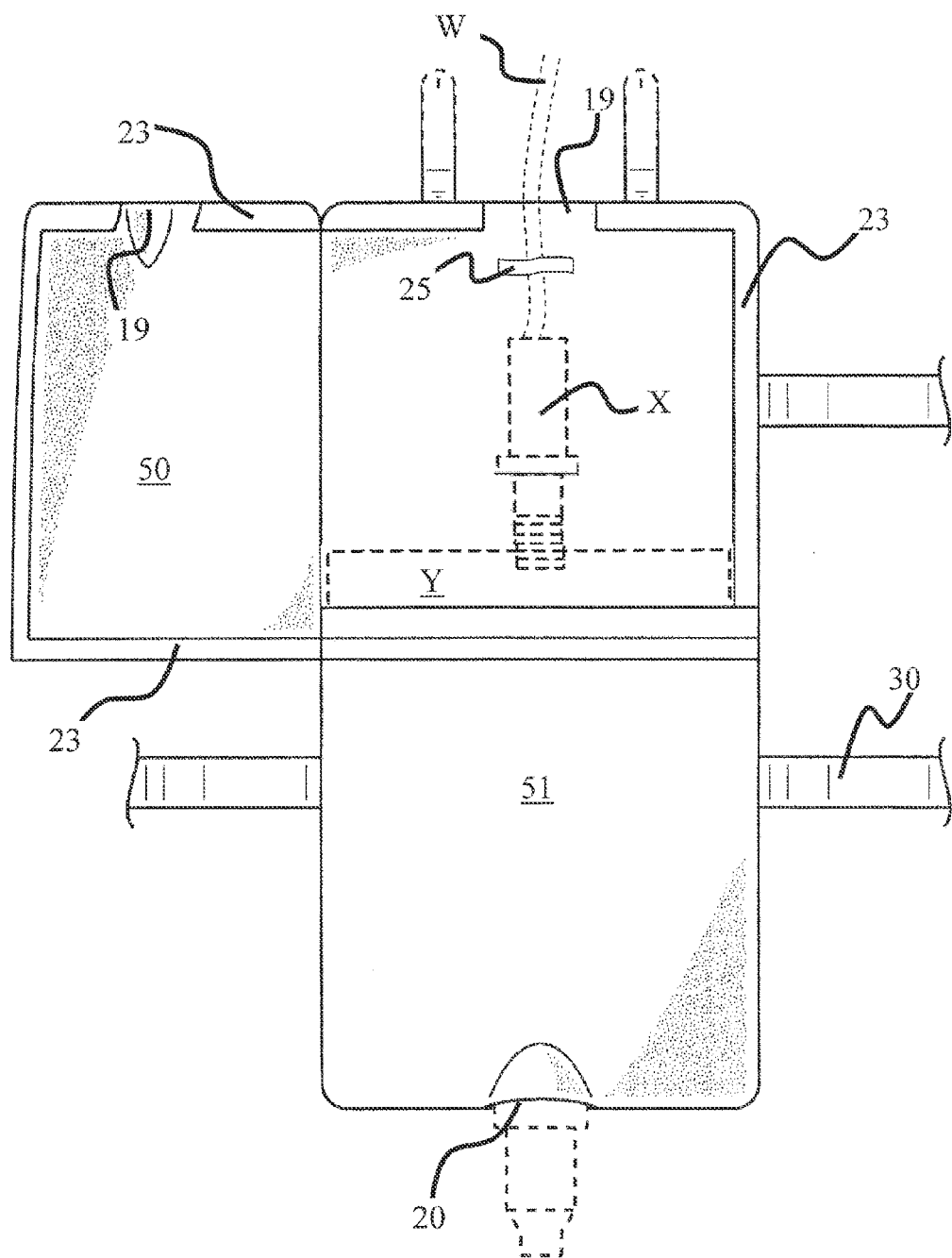
FIG. 6 is an illustration of a front plan view of the embodiment shown in FIG. 2, wherein the urine bag (shown in dotted lines) is shorter and at least one support band is utilized with the tubing.

In a further alternative embodiment, the slot 15 can be made at least partially self-adhering or otherwise made to be closable. In this embodiment, one or more devices or self-closing materials can be employed on the front face interior 14I and/or the rear face interior 16I. In one embodiment, the interiors 14I and 16I, at or near the slot, can be lined with a self-closing material 23 that, when pressed together close all or a sufficient section of the slot, such as, for example, hook and loop material (VELCRO), self-adhesive fabric, flexible magnetic tape, zip seals, and other similar apparatuses, or combinations thereof. FIGS. 2 and 6 show examples of sleeves with self-closing material 23 around the periphery of the slot, as well as around other areas, as will be discussed below. In an alternative embodiment, the interiors 14I and 16I can be configured with one or more closure devices, such as, fir example, hooks, buttons, snaps, zippers, magnetic disks, and similar devices, or combinations thereof.

In an alternative embodiment, the size of the slot itself can be made adjustable. In a further embodiment, the slot, or some portion thereof, can comprise an elastic band that can be used to constrict the size of the slot. The elastic band can be utilized at least with some portion of the proximal end of the slot. When a urine bag is inserted through the slot, the elastic band can temporarily expand, making the slot larger. After the urine bag is disposed within the sleeve, the elastic band can contract, causing the slot 15 to constrict over the proximal end of the urine bag to hold the urine bag within the sleeve. It would be within the skill of a person trained in the art to create or utilize alternative methods and devices for closing the slot. Such variations are considered to be within the scope of the subject invention.

Many urine bags are equipped with at least two valves to accommodate inflow and outflow of urine. An inflow valve X is usually located at or near the top end of the bag and is operably connected to tubing W from the catheter for internal or external contact with the individual. An outflow valve Z is usually located at or near the bottom end for periodically eliminating the contents of the bag. To accommodate these valves, the sleeve 12 of the subject invention can have one or more openings to allow for protrusion or extension of the valves and/or tubing from the cover 10.

In one embodiment, inflow valve X and/or the tubing W can extend through the slot 15 and between two or more security tabs 21, as shown, for example, in FIG. 4A. In another embodiment, shown for example in FIGS. 2 and 6, a self-closing slot can be configured to provide an inflow valve aperture 19, shown, for example, in FIGS. 2 and 6. In still another embodiment, a slot having an elastic band 90 closure can constrict the size of the slot sufficiently to retain a urine bag within the sleeve, but still provide an opening through which the in flow valve X and/or the tubing W can extend.

The urine bag cover 10 of the subject invention can contain, support, and conceal different sizes of leg urine bags. In general, urine leg bags tend to be rectangular in shape, such that the length is greater than the width, making it more amendable to lengthwise attachment to the leg. But, in some instances, the urine leg bags can be more squared in shape. However, the length and other dimensions can vary depending upon the manufacturer. An individual wearing a urine bag may find oneself using different sizes at different times, depending upon one's situation.

As such, the urine bag covers 10 of the subject invention can be made to accommodate a variety of different styles of urine bags. In one embodiment, a cover of the subject invention can be manufactured into a variety of sizes with variable lengths and/or widths to accommodate different size urine bags. However, when shorter length urine bags are used with a cover of the subject invention, the inflow valve may be located within the sleeve rather than extending from the slot 15 or the inflow valve aperture 19. In this situation, the tubing will extend from the slot 15 or an inflow valve aperture 19. To lend support to the tubing or to the inflow valve, and ensure that the security tabs 21, or other slot 15 closure apparatuses do not block, puncture, or otherwise interfere with the tubing and/or inflow valve, at least one support band 25 can be affixed to the sleeve interior 75. So that it can be used with different size tubing and inflow valves, the support band 25 can be adjustable. In a specific embodiment, at least one support band is affixed to the interior rear face 16I. In a further specific embodiment, at least one support band is affixed between approximately 1 inch and approximately 5 inches below the slot 15 and/or inflow valve aperture 19. In more specific embodiment, at least one support band is affixed between approximately 1 inch and approximately 2.5 inches below the slot 15 and/or inflow valve aperture 19.

One of the disadvantages of wearing a urine bag is that it can draw unwanted attention, causing an uncomfortable situation for an individual. A further disadvantage is the fact that urine bags, by necessity, do not conceal their contents. As a result, many individuals who would resume most normal activities refrain from doing so to avoid the stress and embarrassment that may be caused by wearing a non-concealed urine bag.

Advantageously, the cover of the subject invention provides an opportunity to conceal urine bag in such a way that it becomes unobtrusive or, at least, less cause for embarrassment. The various components and/or accessories of the cover of the subject invention, as will be disclosed, can be made or decorated with any of a variety of stylish and/or fun features. This can allow the cover to not only conceal the urine bag, but also act or appear as a stylish accessory.

To aid in the comfort of an individual wearing a cover 10 of the subject invention, it can be beneficial for the sleeve material to have qualities that make it pleasant to maintain against the skin. It can also be beneficial, for a variety of reasons, for the sleeve to be washable. This can include professional or non-professional hand-washing, machine-washing, drycleaning, or any other cleaning method known in the art. In one embodiment, the sleeve material is "breathable", meaning, in general, that it allows at least some air flow between the sleeve and the skin. This can allow for the dissipation of heat between the sleeve and the skin, which can reduce or eliminate sweating between the skin and the sleeve. This can be accomplished by any of a variety of techniques and materials. For example, numerous natural and artificial materials having "sweat wicking" capabilities are well-known in the art. There are also many varieties and styles of mesh, slotted, openweave, or similar materials designed to reduce heat build-up between the material and the skin and reduce sweating therebetween.

In a further embodiment, the sleeve material or materials, or some portion thereof, is waterproof in one embodiment, the sleeve, or some portion thereof, comprises a waterproof material, such as plastic, nylon, vinyl, PVC, or other material(s) that are woven, non-woven, spun, bonded, or otherwise, formed or manufactured. In an alternative embodiment, the sleeve can comprise naturally waterproof materials such as waxes, oils, lanolin, or petroleum-based products. In one embodiment, the sleeve is manufactured of a waterproof material. In an alternative embodiment, the sleeve comprises a material coated or impregnated with a waterproof material.

Given the nature of use and the proximity to the skin of an individual, it is inevitable that the cover 10 will become soiled and susceptible to odors. Odors can be naturally-occurring, but are often the result of bacteria. Thus, as mentioned above, it can be beneficial if the cover and/or sleeve material is amenable to cleaning. In a further embodiment, the cover, sleeve, or portions thereof, comprise one or more materials capable of reducing or preventing the growth of bacteria. In one embodiment, the micro- or macro-structure of the cover material(s) can be such that bacterial growth is inhibited. In an alternative embodiment, the material can be covered, impregnated, or otherwise integrated with an antibacterial substance or product. In yet a further embodiment, the cover can comprise one or more materials that when exposed to particular light frequencies cause a reduction in bacteria.

A person with skill in the art and having benefit of the subject disclosure would well be able to determine any of a variety of materials, or combination(s) of materials with one or more of the above-described qualities of being washable, comfortable, sweat-proof, waterproof, and antibacterial, decorative or stylish, or have other beneficial qualities, that could be utilized with the embodiments of the subject invention. The subject invention is not intended to be limited to any particular material of manufacture, man-made or otherwise. Thus, any and all such variations, not contrary to the disclosed embodiments, are considered to be within the scope of the subject invention.

To secure the cover 10 to the body, one or more straps 30 can be attached to the sleeve. The straps can be attached and/or adjustable so that the cover can be used on the left or right side of the body. They may also be configured so that the cover can be used on any desired part of the body, including, but not limited to, the upper and tower arm and leg. The straps can be fixedly attached or removably attached. In one embodiment, one end of at least two straps is fixedly attached at or about each side of the sleeve, substantially opposite to one another. In a particular embodiment, one end of at least two sets of straps 30 (or 4 straps) are fixedly attached to opposite sides of the sleeve, such that two straps on one side are substantially opposite to two straps on the other side, for example, as shown in FIGS. 1-3. In further embodiments, more than two sets of straps are fixedly attached to the sleeve. In a yet further embodiment, one or more straps are positioned on one side or on opposite sides of the sleeve, but in an offset position. In this embodiment, the distal end of the strap is wound around the body and the strap is removably affixed to the sleeve, as will be described below. In a further embodiment, the ends of the straps not affixed to the sleeve are used to wrap around the body and be removably attached.

Figure 5:
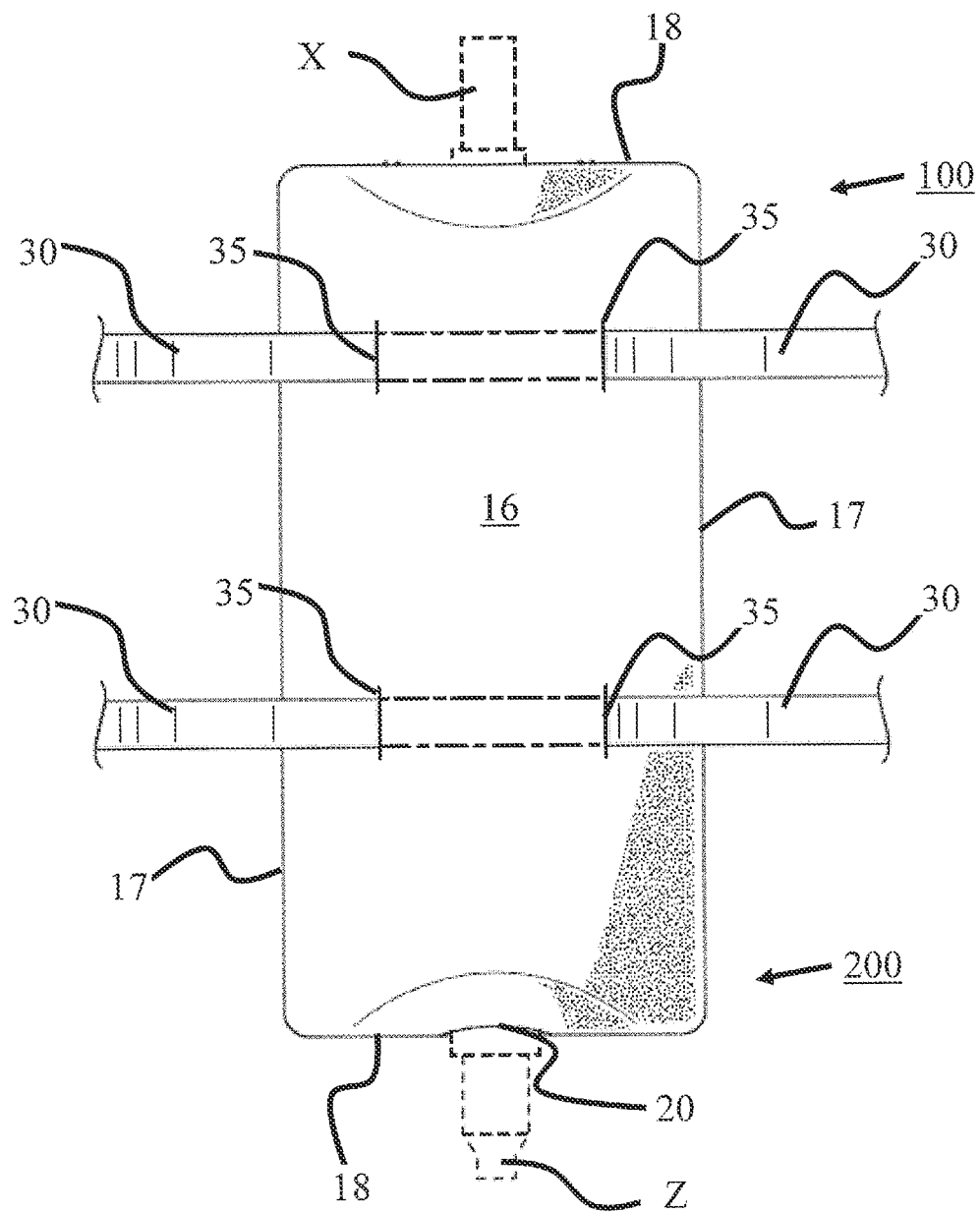
FIG. 5 is an illustration of a rear elevational view of an embodiment of the subject invention. Shown, among other features, are the straps extending through cuts in the rear face of the sleeve.

In an alternative embodiment, the one or more straps can be movably attached to the sleeve such that the location of the sleeve can be moved relative to the straps. FIG. 5 shows an example wherein the straps 30 are fitted through two or more cuts 35 within the sleeve. The cuts 35 can be placed in the front face 14 of the sleeve, but in a more preferred embodiment the cuts are placed in the rear face 16. In this embodiment, a strap is threaded through the two or more cuts, so that the ends extend out to each side of the sleeve. In a further embodiment, a channel or passage can be created on the interior or exterior of the sleeve through which a strap can be threaded between cuts. The channel can comprise the same or different materials as the sleeve or the straps. The use of straps to secure items to the body is well-known in the art. These embodiments described here are all techniques known to those with skill in the art and are considered to be within the scope of the present invention. However, a person with skill in the art would be able to determine any of a variety of methods and techniques for attaching the cover to the body, and such variations are also considered to be within the scope of the present invention.

The straps can have direct contact with the body of the individual. As such, it can be important that the material of the one or more straps be comfortable to wear against the skin and preferably be adjustable to accommodate different individuals. In one embodiment, the straps, or some portion thereof, comprise an elastic or elastic-like material. In another embodiment, the straps comprise a non-elastic material.

The length of the one or more straps can also vary depending upon the type of material, attachment methods, and other factors known to those with skill in the art. In one embodiment, the straps on each side of a sleeve are of different lengths, allowing a first strap to be brought further around the body, for attachment to the second strap. In this embodiment, the first strap is between approximately 10 inches to approximately 36 inches and the second strap is between approximately 5 inches and approximately 15 inches. In a more specific embodiment, the first strap is between approximately 15 inches to approximately 24 inches and the second strap is between approximately 3 inches and approximately 8 inches.

In an alternative embodiment, the straps on each side of a sleeve are of similar lengths, such that they can be overlapped at any point around the body. In this embodiment, the straps are between approximately 15 inches and approximately 36 inches. In a more specific embodiment, the straps are between approximately 10 inches and 24 inches. In a still more specific embodiment, the straps are approximately 20 inches in length. In a further embodiment, the straps are adjustable in length. In a still further embodiment, the straps can be cut to the desired length.

The width of the straps can also vary depending upon several factors known to those with skill in the art. For example, straps of wider widths can be more comfortable to wear, whereas straps of thinner widths might be less cumbersome to manipulate or less prone to cause sweating. In one embodiment, a strap can be of uniform width between the distal and proximal ends. But, in an alternative embodiment, a strap can have variable widths between the distal and proximal ends. In one embodiment, the width of a strap is between approximately 0.5 inch and 4 inches. In a further embodiment, the width of a strap is between approximately 1 inch and 2.5 inches. In a specific embodiment, the strap is approximately 1 inch in width.

The straps 30 can be secured around the body or leg of an individual by any of a variety of devices and methods known in the art. In one embodiment, the straps are tied together. In another embodiment, a strap on one side of the sleeve is removably attached to a corresponding strap on the other side of the sleeve, or directly to the sleeve as described above, with one or more of various connecting devices, such as, for example, buttons, snaps, hooks, clasps, buckles, pressure mechanisms, and similar connecting devices. In an alternative embodiment, a strap on one side of the sleeve is removably attached to a corresponding strap on the other side of the sleeve, or directly to the sleeve, by utilizing hook and loop (such as VELCRO) material. In a still further alternative embodiment, a strap on one side of the sleeve is removably attached to a corresponding strap on the other side of the sleeve, or directly to the sleeve, by utilizing a self adhering fabric. It should be understood that the use of straps or strapping and associated devices or methods for securing articles to an individual are well-known in the art. Substitution of straps and attachments therefore, other than those specifically exemplified herein, are contemplated to be within the scope of the present invention.

A concern that unavoidably accompanies using a urine bag is the position and stability of the catheters, particularly indwelling catheters, and associated tubing that leads to the urine bag. If the tubing is kept too firmly attached to the body and without sufficient length free for movement, a catheter can be pulled or dislodged. Likewise, if the tubing remains too loose, it can be prone to getting caught on clothing or nearby structures and/or excessive movement, e.g., swinging, bouncing, twisting, etc., of the tubing can pull or dislodge a catheter. In addition, the inflow valve on full-size urine bags can extend through the slot 15 and rest against the skin, which can be uncomfortable.

Figures 7, 8:
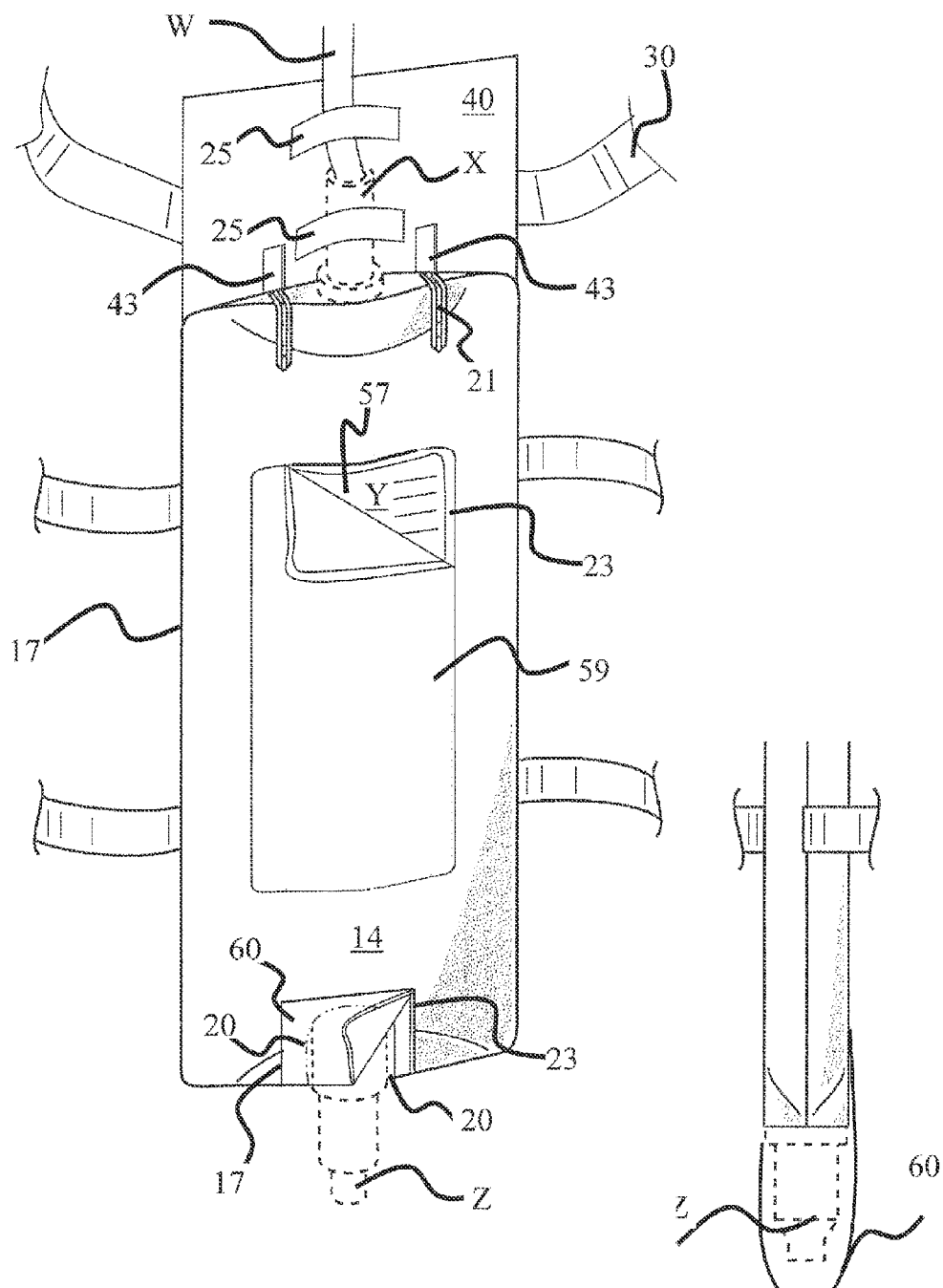
FIG. 7 is an illustration of a front perspective view of an embodiment that includes a sleeve window and sleeve window cover, a collar, and an outflow valve overlay.
FIG. 8 is an illustration of a side plan view of an embodiment wherein the outflow valve overlay extends over the entire outflow valve.

To assist with stabilizing the tubing and to prevent the inflow valve of a urinary bag from direct contact with the skin, the urine bag cover 10 of the subject invention can include a collar 40. In one embodiment, the collar is, in general, a flange extending from the proximal end 100 of the sleeve, as shown, for example, in FIG. 7. In one embodiment, the collar 40 comprises the same material(s) as described above for the sleeve. In an alternative embodiment, the collar comprises a different material(s) than that utilized for the sleeve. Some individuals may prefer not to use the collar. In one embodiment, the cover is flexible, so that it can be folded over the front face exterior 14E or the rear face exterior 16E. In an alternative embodiment, the cover can have one or more notches 43 that correspond to the location(s) of one or more security tabs 21, or other apparatus used to close the slot 15 of the sleeve. FIG. 7 illustrates an example of a collar 40 with notches 43. The notches can allow the collar to be folded into the sleeve interior 75, yet still be used to close the slot. In an alternative embodiment, the collar can be removable from the sleeve. In this embodiment, the collar can be operably attached to the sleeve by any of a variety of methods and devices, including ties, snaps, buttons, hook and loop, zipper, zipper seal, or any other method disclosed herein or known to those with skill in the art. In order that the collar can maintain position and shape against the body of an individual, the collar can employ one or more rigid or semi-rigid materials. In one embodiment, the collar or some portion thereof can be manufactured of a rigid or semi-rigid material. In an alternative embodiment, a structure made of rigid or semi-rigid material can be attached to the collar. In a further alternative embodiment, at least one strap 30, as described above, is attached to the collar for securing the collar against the body. In a particular embodiment, least two straps, oppositely attached at or near the side edge 17 of the collar are used to secure the collar against the body. In an alternative embodiment, at least 4 straps, oppositely attached in pairs at or near the side edge of the collar are used to secure the collar against the body.

To secure the tubing W and/or the inflow valve X to the collar 40, one or more support bands 25 can be attached to the collar, an example of which is shown in FIG. 7. The tubing going into the inflow valve can be threaded between the collar and the one or more support bands. Also, one or more support bands can be located on the collar such that the inflow valve can also be supported against the collar. Use of the collar and corresponding support bands can help support the tubing and reduce or eliminate extraneous movement. In a further embodiment, the support bands are adjustable to accommodate different diameter tubing and inflow valves. In a specific embodiment, the collar makes use of two support bands 25, as shown for example, in FIG. 7.

Typically, when a urine bag is inserted into a sleeve 12 of the subject invention, the outflow valve Z can protrude from the outflow valve aperture 20. This can be uncomfortable against the body. In a further embodiment, a flow valve guard 26 can be incorporated with the sleeve to reduce or prevent such contact. In one embodiment, a flow valve guard extends below the distal edge of a sleeve, such as shown, for example, in FIG. 10. A flow valve guard 26 can extend completely across, i.e., from one side edge 17 to another side edge 17, the distal end of a sleeve. Alternatively, a flow valve guard can extend partially across the distal end of a sleeve. It can be preferable for the flow guard valve to extend sufficiently across the distal end that it inhibits an outflow valve from contacting the body during normal activity. Further, outflow valves of different urine bag styles can have different dimensions, such that they can extend at different lengths from an outflow valve aperture. Thus, the flow guard valve can extend distally from the sleeve to any length that inhibits contact of an outflow valve with the body. Thus, if an outflow valve Z protrudes from the outflow valve aperture 20, the flow valve guard dimensions will ensure that it is positioned between the body and the flow valve, so that they do not make contact. In a further embodiment, one or more support bands 25 can also be utilized with a flow valve guard to secure a flow valve against the flow valve guard.

Also, certain other features discussed above with regard to a collar 40 can be equally applicable to a flow valve guard 26. For example, a notch 43 could also be utilized with a flow valve guard to accommodate the outflow valve, an example of which is shown in FIG. 10. Such applicable features are reiterated here with regard to the embodiments of a flow valve guard. Further, the factors that can be considered by those skilled in the art with regard to the choice of materials for the collar and other components of the embodiments of the subject invention have been discussed above and are reasserted here with regard to the outflow valve aperture.

Under certain circumstances or with specific medical conditions, it can be necessary or desirable for an individual to monitor urine output. The quantity of urine output and the appearance thereof can be indicative of positive or negative factors pertaining to health and/or recovery. Consequently, most urine bags are made of clear or semi-clear material(s) and, further, are marked with graduations indicating volume.

A unique advantage of the urine bag cover 10 of the subject invention is that it includes a sleeve window 57, that is, in general, an opening within the sleeve that allows the urine bag and contents to be viewed without compromising the privacy of the individual or removing the urine bag from the cover. The sleeve also includes a sleeve window cover that conceals or covers, at least, the sleeve window and can cover other portions of or structures of a sleeve. In one embodiment, the sleeve window cover is configured as a sleeve flap 50, where the front face 14 of the sleeve is divided into two or more sections, for example, as shown in FIGS. 1-3, 4C, 4D, and 6. With this embodiment, the bottom most section 51 can be attached to the rear face 16. It can be preferable for the bottom most section 51 to be fixedly attached to the rear face 16 on at least the distal end 200 to ensure closure at that end and that the urine bag cannot come out accidentally. In a further embodiment, at least one other section of the sleeve front face is configured as the sleeve flap 50 that can be opened and closed as desired, as shown, for example, in FIGS. 2 and 6. The sleeve flap 50, when open, presents substantially a sleeve window 57 that allows the urine bag to be visible and monitored and can also assist with placement of the urine bag in the sleeve. When closed the sleeve flap acts as a sleeve window cover. The sleeve flap can be removably attached to the rear face 16 such that each side can be opened and closed for viewing, allowing the sleeve flap to be removed from the cover. In an alternative embodiment, at least one side, or a portion thereof, of the sleeve flap can be fixedly attached to the rear face 16, with the remaining sides removably attached, an example of which is shown in FIGS. 2, 3, and 6. The sleeve flap 50 can be removably attached by a variety of methods and devices known in the art and previously described herein. In a particular embodiment, the sleeve flap is removably attached to the rear face by the use of self-closing material 23, mentioned previously, such as, for example, hook and loop material (VELCRO), self-adhesive fabric, flexible magnetic tape, zip seals, and other similar means, or combinations thereof, located on all or some portion of the edges of the sleeve.

An alternative embodiment employs a smaller sleeve window 57 within the front face 14 of the sleeve. In general, the sleeve window can be a cut-out in the front face of the sleeve. In this embodiment, shown for example, in FIG. 7, the front face of the sleeve has an opening cut-out or otherwise formed that allows at least a portion of a urine bag therein to be visible and monitored. A sleeve window 57 can be placed at any location within the front face of the sleeve, such as in the center, or closer to a side or end of the sleeve. In one embodiment, the location of the sleeve window allows volumetric gradations, urine color, or any other indicators on the urine bag to be visible. The dimensions of the sleeve window can depend upon several factors, including, but not limited to, the dimensions of the sleeve and/or front face, location in the front face, and size of the urine bag used therein. In one embodiment, the sleeve window has the same or similar shape as the sleeve, but is proportionally smaller, such as shown, for example, in FIG. 7. The sleeve window can also have any of a variety of other circumferential shape configurations, including, but not limited to, round, star, square, oval, triangle, rectangle, or any other polygonal shape. In an alternative embodiment, the sleeve window has a shape that is different than the shape of the sleeve.

In a further embodiment, a sleeve window has a fenestra 58 therein that permits viewing of the interior of a sleeve, but inhibits contact with the interior. The fenestra 58 can prevent contact with a urine bag within the sleeve. A fenestra can also provide additional support to prevent a urine bag from bulging through a sleeve window, particularly when full. Ideally, the fenestra does not inhibit viewing or monitoring of the urine bag. It can also be beneficial for a fenestra to be semi-rigid or have sufficient flexibility that it can bend or curve in response to changes in a urine bag shape as it fills, but also prevent a urine bag from bulging or protruding through the sleeve window. In one embodiment, a fenestra is a clear covering within the sleeve window, in an alternative embodiment, the fenestra is a screen or mesh-like material, such as shown, for example, in FIG. 10. Variations in a fenestra can be determined by a person skilled in the art. Such variations are within the scope of the subject invention.

In a further embodiment, a sleeve window patch 59 is utilized to conceal the sleeve window 57 when not in use for monitoring the urine bag. The sleeve window patch 59 can be fixedly or removably attached, or some combination thereof to the front face. The sleeve window patch 59 can also be positioned so that it can cover at least a portion of but preferably the entire sleeve window. FIG. 7 illustrates one example of a sleeve window patch embodiment of the subject invention. In one embodiment, at least one edge of, or portion thereof, the sleeve window patch 59 is fixedly attached to the front face 14, or some other area of the cover. In a further embodiment, at least one other edge of the sleeve window cover is removably attached to the front face. In an alternative embodiment, each edge of sleeve window patch 59 is removably attached so that it can be removed from the front face. The sleeve window patch can be configured in any of a variety of circumferential shapes, including, but not limited to round, star, square, oval, triangle, rectangle, or any other polygonal shape. In one embodiment, the circumferential shape of the sleeve window patch is the same as or similar to the circumferential shape of the sleeve window. In an alternative embodiment, the sleeve window has a shape that is different than the shape of the sleeve.

Figure 9:
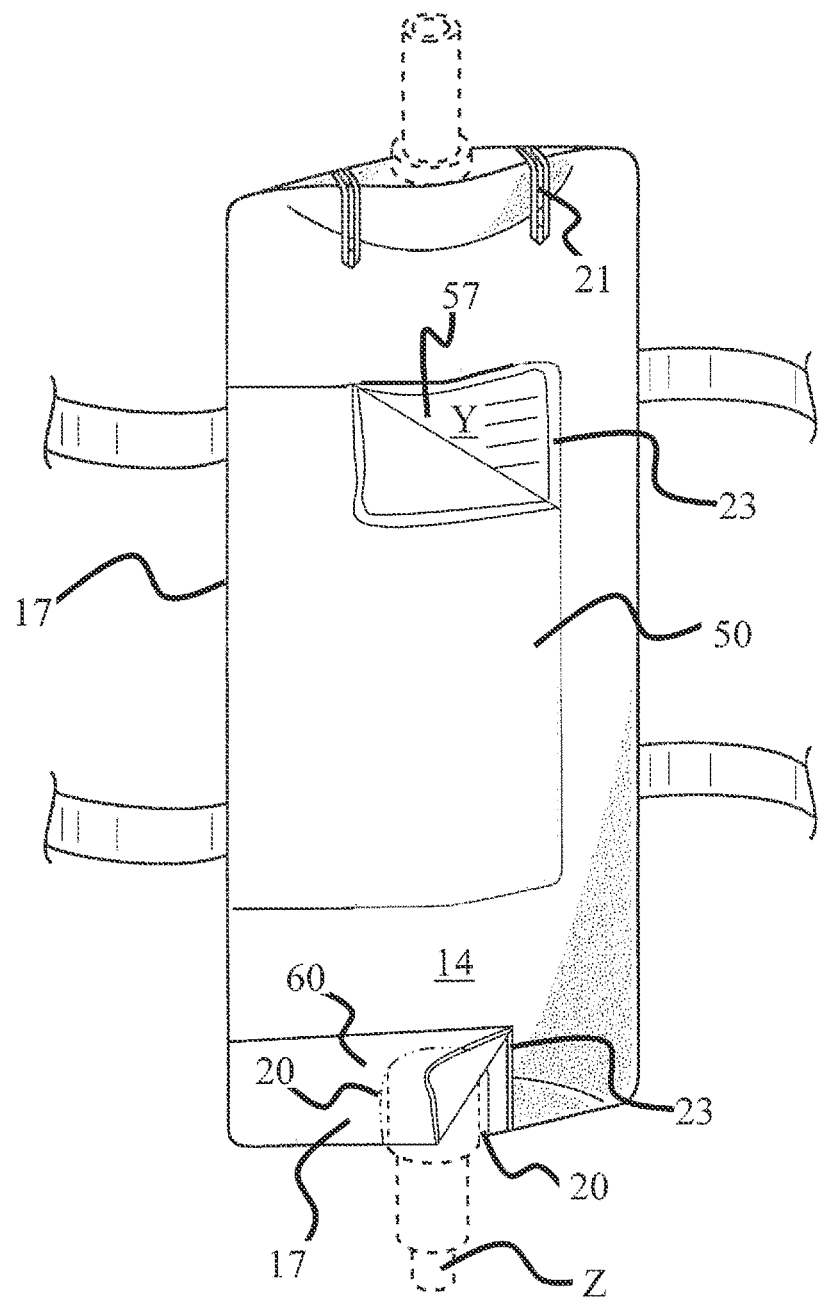
FIG. 9 is an illustration of a front perspective view of an embodiment wherein a sleeve window and an outflow valve aperture are each covered by sleeve flaps attached to the side of the sleeve.

An alternative embodiment utilizes a combination of the sleeve window flap and the sleeve window. In this embodiment, a sleeve window flap is fixedly attached along one edge to the cover and extends over a sleeve window. FIG. 9 shows an example of such an embodiment. It would be within the skill of a person trained in the art and having benefit of the subject disclosure to devise various alternative sleeve windows and sleeve window coverings. It is contemplated that such alternatives would be within the scope of the subject invention.

Figure 4B:
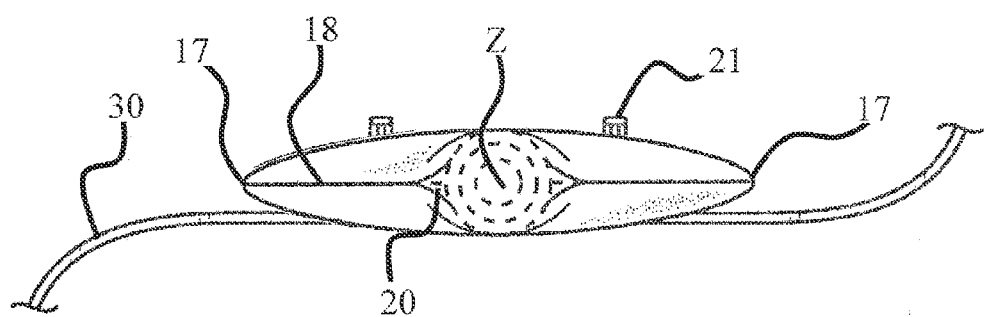
Figure 4C:
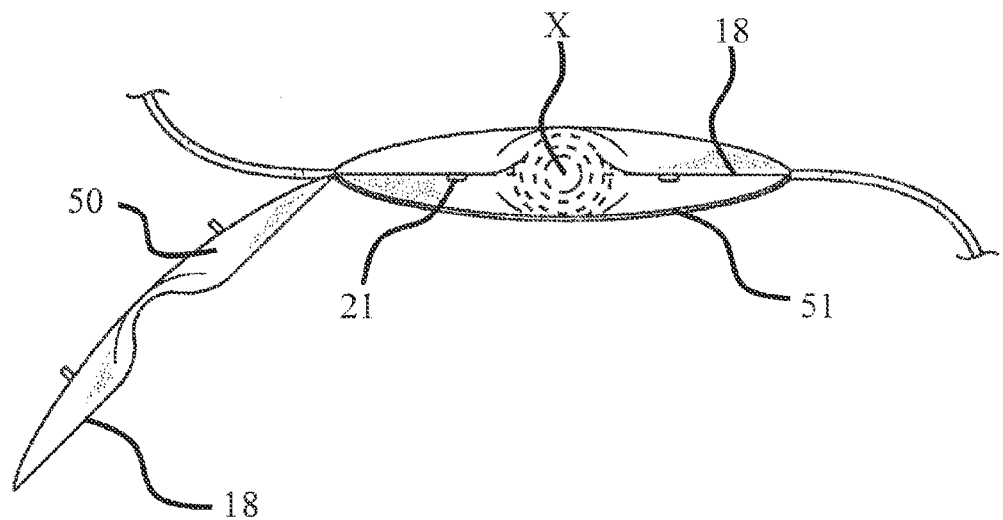
Figure 4D:
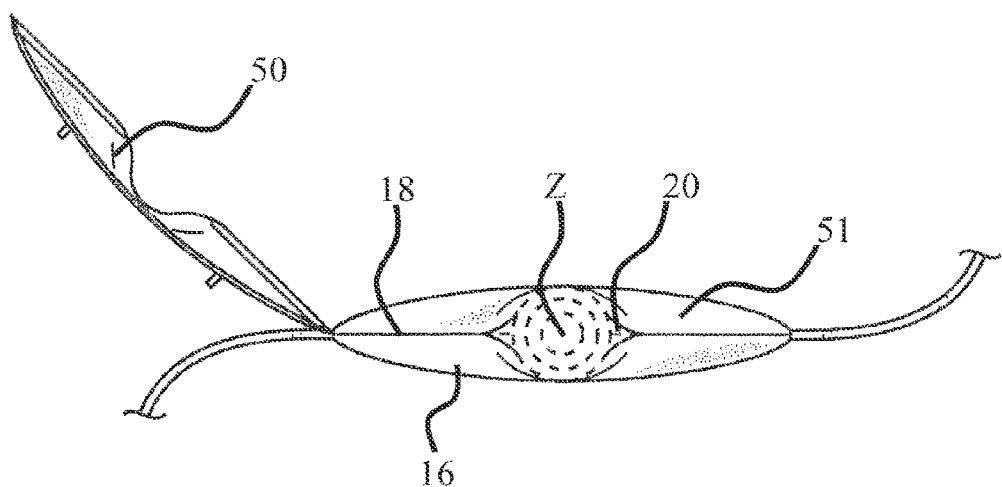

While most urine bags are disposable, they are usually designed with an outflow valve Z, so that they can be emptied periodically between replacements. The outflow valve is usually located at or near the distal end 200 of the urine bag and usually extends from the urine bag. To accommodate the outflow valve and allow the urine bag to be emptied without removal from the urine bag cover 10, an outflow valve aperture 20 can be included at or near the distal end 200 of the cover. As shown, for example, in FIGS. 1 and 4B, when the urine bag is placed within the urine bag cover, the outflow valve Z can be extended through the outflow valve aperture 20.

Not all urine bags have the same configurations. In addition to size differences in urine bags, different manufactures can utilize different types or styles of inflow or outflow valves. For example, the outflow valves on some urine bags often utilize outflow valve controls, such as, by way of example, a lever, knob, switch, or other flow control device on the outflow valve. Often these control devices are positioned at the distal end 200 of the urine bag, just above the drainage tube. As such, the dimensions and location of the outflow valve aperture should be sufficiently large enough to allow access to a control device.

In one embodiment, the outflow valve aperture 20 is located at the distal end 200 of the cover and extends towards the proximal end 100 of the front face 14 a sufficient distance to allow access to any control device on the outflow valve. In a further embodiment, the outflow valve aperture is positioned at about the center of the distal end and extends upwards along about the center of the front face, as shown, for example, in FIG. 7. In a particular embodiment, the outflow valve aperture 20 extends from the distal end of the sleeve towards the proximal end, between approximately 1 inch and approximately 3 inches. In a more particular embodiment, the outflow valve aperture 20 extends from the distal end of the sleeve towards the proximal end, between approximately 1 inch and approximately 1.5 inch.

To assist with securing the control device on the urine bag and provide additional privacy to an individual, an outlet valve overlay 60 can be used to cover all or some portion of the outflow valve aperture 20. An outlet valve overlay 60 can be similar to a sleeve window patch 59, discussed above, in that it can be fixedly or removably attached, or some combination thereof, to the front face, and possibly, the distal end of the cover and/or the distal end of the rear face. Preferably, the outlet valve overlay 60 is easily manipulated with the use of quick-release attachments, so that it does not hinder the process of draining the urine bag. The valve overlay 60 can be positioned so that it can cover at least a portion of, or the entire outflow valve aperture 20. In one embodiment, the valve overlay 60 is fixedly attached to the front face 14 along at least one edge or a section thereof. In a further embodiment, at least one other edge of the valve overlay is removably attached to the front face. In an alternative embodiment, each edge of valve overlay is removably attached, so that it can be removed from the front face.

As mentioned previously, the outflow valve Z on the urine bag Y can extend out from the urine bag cover 10 through the outflow valve aperture 20. To further protect the outflow valve and lend still more privacy to the individual, the outflow valve overlay 60 can be substantially elongated so as to cover the outflow valve Z. Alternatively, the outflow valve overlay can be sufficiently elongated so as to wrap over the distal end 200 of the outflow valve and attach to some point on the rear face 16. FIG. 8 shows an embodiment wherein the outflow valve overlay is removably attached to the front face 14 and fixedly attached to the rear face 16. This embodiment, when in use, can cover the outflow valve Z and outflow aperture 20. To use the outflow valve, the valve overlay 60 can be disconnected from the front face to expose the outlet valve and any flow control devices associated therewith.

As with the sleeve window patch 59, the outflow valve overlay can be removably attached by a variety of methods and devices known in the art and previously described herein. In a particular embodiment, the valve overlay is removably attached to the front face exterior 14E by the use of self-closing material 23, mentioned previously, such as, for example, hook and loop material (VELCRO), self-adhesive fabric, flexible magnetic tape, zip seals, and other similar means, or combinations thereof, located on all edges or some portion of the edges of the overlay.

In a specific embodiment, the outflow valve overlay 20 is fixedly attached along a proximal end or edge to the front face exterior 14E above the outflow valve aperture. In a further specific embodiment, the outflow valve overlay extends to the distal end of the sleeve. In a still further specific embodiment, the side edges 17 are removably attached to the front face exterior 14E utilizing a quick-release mechanism. In a further embodiment, the quick-release mechanism is hook and loop (VELCRO) material.

In another specific embodiment, the outflow valve overlay 60 has at least one edge fixedly attached to the cover. In one embodiment, at least one edge of an outflow valve overlay is fixedly attached to a side edge 17 of a cover. In a further embodiment, the outflow valve overlay extends over the front face 14 to cover the outflow valve aperture 20 and any outflow valve extending therefrom. In a further embodiment, the outflow valve has at least one other edge that is removeably attached to the front face. Such attachment can utilize a quick-release mechanism, such as, but not limited to, hook and loop (VELCRO) material.

The outflow valve overlay 60 can be configured in any of a variety of circumferential shapes, including, but not limited to round, star, square, oval, triangular, rectangle, or any other polygonal shape. In one embodiment, the circumferential shape of the valve overlay is the same as or similar to the circumferential shape of the outflow valve aperture. In an alternative embodiment, the valve overlay has a shape that is different than the shape of the outflow valve aperture.

Figure 11:
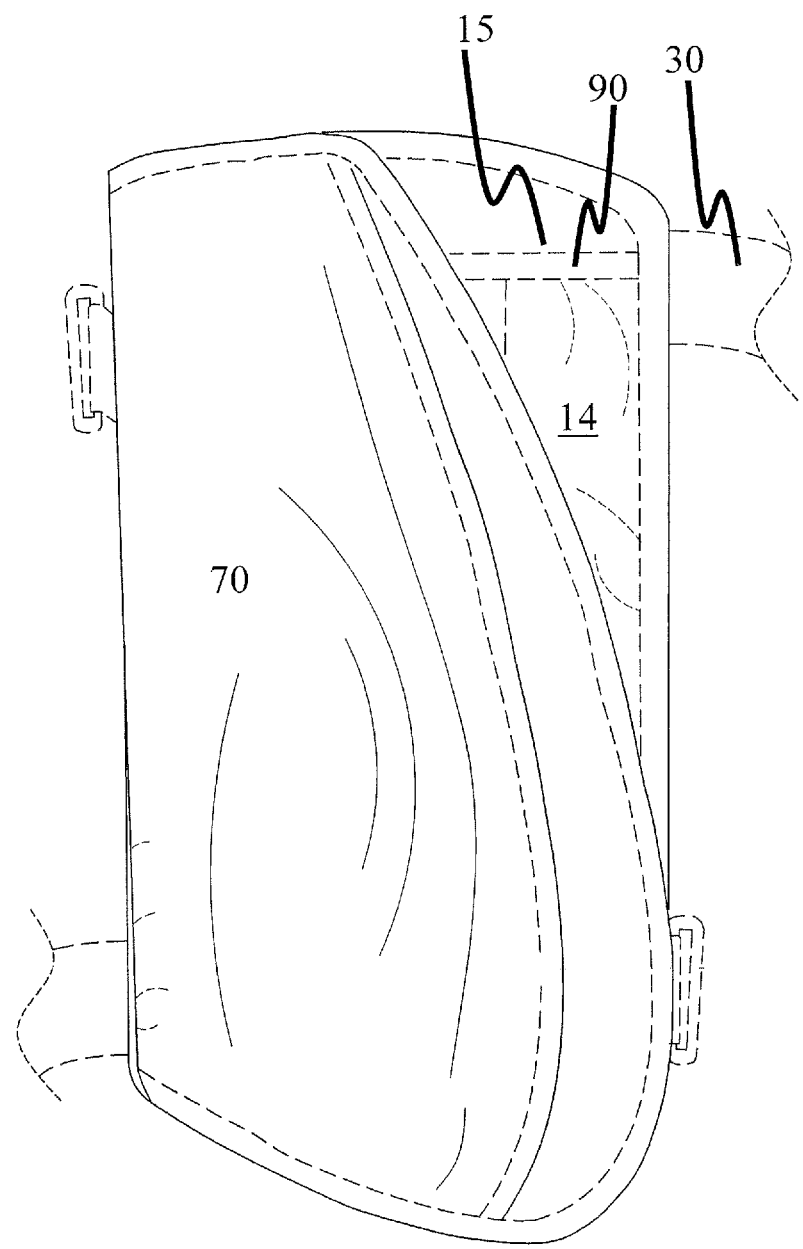
FIG. 11 is an illustration of a front elevation view of an alternative embodiment of a urine bag cover having a front face cover, according to embodiments of the subject invention. In this view, the front face cover is shown covering the front face of the sleeve, including the sleeve window cover and outflow valve aperture.

From the description above, it can be seen that it can be advantageous to have a sleeve cover and an outflow valve overlay. However, it can be more advantageous if the sleeve interior, sleeve window, outflow valve aperture (and a valve therein) and other components of a sleeve be viewed or accessible without having to manipulate multiple covers or overlays. In one embodiment, a sleeve window flap 50 is combined with an outflow valve overlay 60. In a more specific embodiment, a sleeve window flap is enlarged or extended towards the distal end 200, so that it can cover a sleeve window, as well as an outflow valve aperture 20, to form a front face cover 70. FIGS. 11 and 12 illustrate one embodiment of a front face cover. A front face cover 70 can have all of it edges removeably affixed to the front face. This would allow any one or more of the edges to be removed from the sleeve so that a sleeve window 57 could be viewed or an outlet valve aperture can be exposed. This embodiment would also allow the entire front face cover to be removed from a sleeve 10.

In an alternative embodiment, a front face cover 70 can have at least one edge that is fixedly attached to a sleeve and at least one other edge that is removeably attached to a sleeve. In a particular embodiment, a front face cover has one edge that is fixedly attached to, or at about, a side edge and at least one other edge that is removably attached to, or at about, another side edge 17. In a further embodiment, a front face cover has at least two edges that are removably attached to a sleeve. In a still further embodiment, at least one edge is removably attached to a distal edge of the sleeve. In yet another embodiment, at least one edge of a front face cover 70 is removably attached to the distal edge of a flow valve guard 26

The front face cover can have a longitudinal extent (i.e., length from the proximal end 100 to the distal end 200) sufficient to cover all or most of a sleeve window, as well as all or most of an outlet valve aperture. As described above, the valve of a urine bag can protrude from an outlet valve aperture. In a further embodiment, the front face cover has a longitudinal extent that can further cover an outflow valve Z of a urine bag protruding from an outlet valve aperture 20. In a particular embodiment, the longitudinal extent of a front face cover can be from at or about the slot 15 to at or about the distal end of a flow valve guard 26. In an alternative particular embodiment, the longitudinal extent of a front face cover can be from at or about the proximal end of a collar 40 to at or about the distal end of a flow valve guard 26. FIG. 12 shows an embodiment of a front face cover where a portion of the proximal end extends to about the proximal end of a collar and another portion of the front face cover curves towards the slot 15.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention has been described herein in considerable detail, in order to comply with the Patent Statutes and to provide those skilled in the art with information needed to apply the novel principles, and to construct and use such specialized components as are required. However, it is to be understood that the invention can be carried out by specifically different equipment and devices, and that various modifications, both as to equipment details and operating procedures can be effected without departing from the scope of the invention itself. Further, it should be understood that, although the present invention has been described with reference to specific details of certain embodiments thereof, it is not intended that such details should be regarded as limitations upon the scope of the invention except as and to the extent that they are included in the accompanying claims.

I claim:

1. A urine bag cover comprising:
a sleeve having a front face, a rear face, a distal end with an outlet valve aperture and a proximal end with a securable sleeve slot, such that the urine bag is fully insertable within the sleeve and the sleeve slot can be at least partially closed over the urine bag;
a sleeve window within the sleeve that allows the sleeve interior and any contents therein to be at least partially visible;
a front face cover having one edge, at least partially, fixedly attached at or in proximity to a side edge of the sleeve and, at least one other edge of the front face cover that is at or in proximity to another edge of the sleeve and at least partially removable from the sleeve, such that the front face cover, when emplaced over the front face of the sleeve, inhibits at least the viewing of the sleeve interior through the sleeve window and access to the outlet valve aperture, wherein removal of the one other edge of the front face cover from the sleeve allows viewing of the sleeve interior through the sleeve window and access to the outlet valve aperture; and
at least one strap operably connected to the sleeve.

2. A cover according to claim 1, further comprising one or more structural features that allow the sleeve to expand.

3. A cover according to claim 2, wherein at least a portion of the sleeve comprises a deformable material.

4. A cover according to claim 2, wherein the structural features comprise one or more pleats, folds, or tucks.

5. A cover according to claim 4, wherein the structural features are located on the front face.

6. A cover according to claim 5, further comprising a fenestra within the sleeve window that allows viewing of the sleeve interior.

7. A cover according to claim 6, wherein the fenestra is a mesh-like material that allows viewing of the sleeve interior.

8. A cover according to claim 6, wherein the front face cover is completely removable from and replaceable on the sleeve.

9. A cover according to claim 6, wherein the front face has at least two edges that are removably attached to the sleeve.

10. A cover according to claim 9, wherein at least one removably attached edge is removably attachable to a side edge of the sleeve that is opposite from the fixedly attached edge of the front face cover and at least one other removably attached edge is removably attachable to a distal end edge of the sleeve.

11. A cover according to claim 1 wherein the front face cover extends distally sufficiently to further cover an outflow valve protruding from the outflow valve aperture.

12. A cover according to claim 11, wherein the sleeve slot is secured with an elastic band that allows the sleeve slot to expand and constrict in size.

13. A cover according to claim 11, further comprising a flow valve guard.

14. A cover according to claim 13, further comprising one or more support bands on the flow valve guard to secure the outflow valve.

15. A cover according to claim 13, further comprising a collar.

16. A cover according to claim 15, wherein the front face cover extends proximally sufficiently to at least partially cover the collar.

17. The cover, according to claim 13, comprising at least two pairs of straps operably connected to the cover.

18. A cover according to claim 6, wherein the fenestra is a clear covering over the sleeve window that allows viewing of the sleeve interior.

19. A cover according to claim 11, further comprising a flow valve guard to inhibit contact with the outlet valve on the urine bag.

20. A cover according to claim 19, wherein the front face cover extends from and covers at least part of the slot and extends distally to cover all or most of the flow valve guard.

* * * * *